United States Patent [19]
Stevens et al.

[11] Patent Number: 5,620,639
[45] Date of Patent: Apr. 15, 1997

[54] METHOD OF MANUFACTURING NEEDLES

[76] Inventors: John F. Stevens, 29 Somers Rd., Warrandyte, Victoria 3113; Trevor G. Smith, 142 Lamond Ave., Kilsyth, Victoria 3137; Jack H. Bartlett, 11 Nicholas Ave., Glen Waverley, Victoria 3150, all of Australia

[21] Appl. No.: 513,920
[22] PCT Filed: Mar. 9, 1994
[86] PCT No.: PCT/AU94/00109
§ 371 Date: Oct. 17, 1995
§ 102(e) Date: Oct. 17, 1995
[87] PCT Pub. No.: WO94/20279
PCT Pub. Date: Sep. 15, 1994

[30] Foreign Application Priority Data

Mar. 9, 1993 [AU] Australia ............... PL7719

[51] Int. Cl.$^6$ ................... B29C 44/02
[52] U.S. Cl. ............. 264/85; 264/504; 264/572
[58] Field of Search .............. 264/85, 504, 572, 264/500

[56] References Cited

U.S. PATENT DOCUMENTS

| | | | |
|---|---|---|---|
| 4,020,837 | 5/1977 | Larson | 604/411 |
| 4,058,121 | 11/1977 | Choksi et al. | 604/411 |
| 5,225,141 | 7/1993 | Hendry | 264/572 |
| 5,454,409 | 10/1995 | McAffer et al. | 141/329 |

FOREIGN PATENT DOCUMENTS

| | | |
|---|---|---|
| 33222/93 | 8/1993 | Australia . |
| 174011 | 3/1986 | European Pat. Off. . |
| 271775 | 6/1988 | European Pat. Off. . |
| 447726 | 9/1991 | European Pat. Off. . |
| 2164363 | 5/1973 | Germany . |
| 50-71756 | 6/1973 | Japan ........................... 264/572 |
| 5-208460 | 8/1993 | Japan ........................... 264/572 |
| 1644968 | 4/1991 | U.S.S.R. . |
| WO87/01673 | 3/1987 | WIPO . |

OTHER PUBLICATIONS

Derwent Abstract Accession No. 75401B/42, Class A32, CH,A, 613399 (Buhler Gebr AG) 28 Sep. 1979 (28.09.79), Abstract.

Derwent Abstract Accession No. 92-214538/26, Class A32, NL,A, 9002483 (Wavin BV) 1 Jun. 1992 (01.06.92), Abstract.

*Primary Examiner*—Catherine Timm
*Attorney, Agent, or Firm*—Merchant, Gould, Smith, Edell, Welter & Schmidt, P.A.

[57] ABSTRACT

A method of manufacturing an integral one-piece needle, the method comprising feeding a polymeric resin into a mould cavity and injecting a fluid under pressure into at least a portion of the cavity to eject therefrom the central region of the polymeric resin. This creates an annulus of polymeric resin having an orifice therethrough, the annulus of polymeric resin forming the cannula of the needle, the mounting hub being provided by the remaining portion of the cavity.

15 Claims, 3 Drawing Sheets

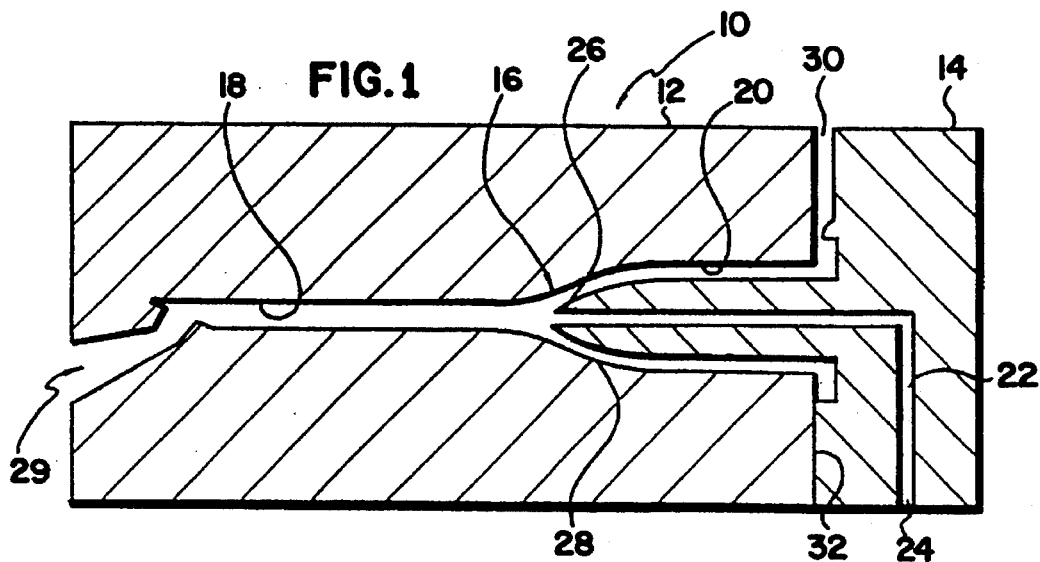
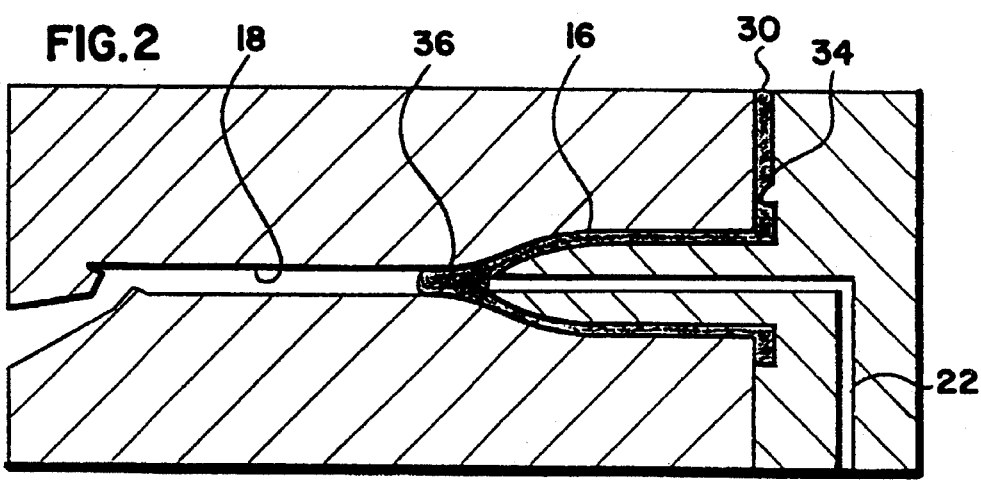
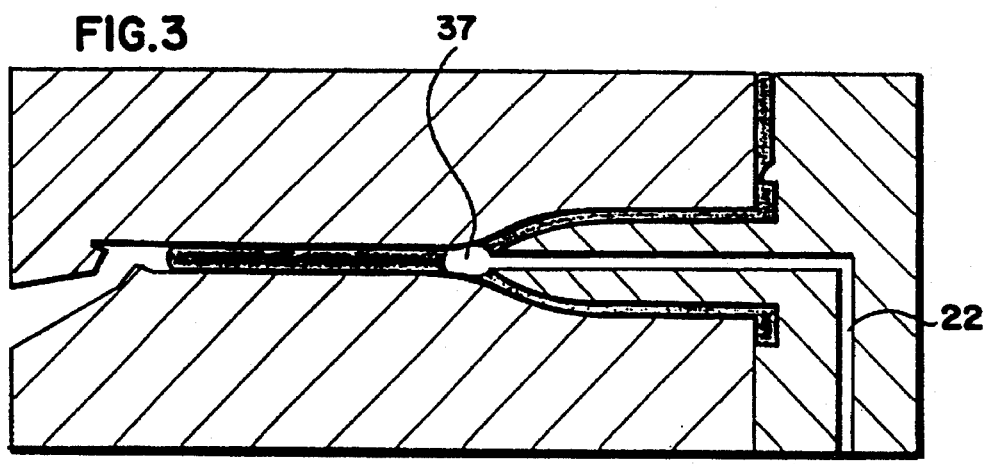

METHOD OF MANUFACTURING NEEDLES

THIS INVENTION relates to a new method of manufacturing needles. In particular, the invention relates to needles suitable for use in the irrigation or aspiration of serums or liquids into or from human bodies or any other living bodies or materials. However, it will of course be understood that the invention is not to be limited to needles only usable for these particular uses.

Conventional needles are traditionally formed from more than one component. Typically, these needles comprise a steel cannula and a plastic or metal mounting hub rigidly secured thereto. An adhesive is often utilised as a third component to secure the cannula to the hub.

In these conventional needles there is clearly a manufacturing expense in producing separate components and in subsequently securing those components together. There is thus a need to remove manufacturing difficulties and to be able to more rapidly and more efficiently produce large numbers of needles.

The present invention relates to a method of manufacturing integral one-piece needles so that the difficulties associated with forming needles from more than one component are overcome, or at least partially alleviated. The present invention is characterised by the use of fluid-assisted injection moulding processes.

Fluid-assisted injection moulding comprises a partial injection of a polymer melt to a mould cavity, followed by an injection of a fluid such as compressed gas into the core of the polymer melt. During the gas injection, the gas normally takes the path of least resistance to catch up to the melt front where, if the mould is properly vented, the pressure is lowest. In principle, the gas penetrates and hollows out the network of gas channels, displacing molten polymer at the hot core to fill the entire cavity.

However, this type of process has only been recognised as being capable of producing large parts with thick sections to attain structural rigidity without sacrificing good surface quality (see an article by L S Turng in "Advances in Polymer Technology" from the Journal of the Polymer Processing Institute, titled "Development and Application of CAE Technology for the Gas-Assisted Injection Moulding Process").

The present invention provides a method for manufacturing an integral one-piece needle, the method being characterised by feeding a polymeric resin into a mould cavity and injecting a fluid under pressure into at least a portion of the cavity to eject therefrom the central region of the polymeric resin, creating an annulus of polymeric resin having an orifice therethrough, the annulus of polymeric resin forming the cannula of the needle, the mounting hub being provided by the remaining portion of the cavity.

The fluid injection may be initiated either before or after the cavity is filled. The injection of the fluid before the cavity is filled results in the method of the invention operating similarly in principle to the fluid-assisted injection moulding techniques described above; namely, the fluid assists in pushing the melt through the cavity.

However, the injection of the fluid after the cavity is filled requires the cavity to include an aperture therein (in the form of an exit channel) which allows the expulsion of the displaced molten central region of the polymer.

The moulding process of the present invention preferably utilises conventional moulding machinery, such as injection moulding machinery, to feed the polymeric resin into the mould. In this respect, the mould preferably has a construction such as to allow the passing of fluid under high pressure separate to the means of injecting or feeding the polymeric resin into the mould.

It will also be appreciated that various design guidelines will need to be followed and considered in order to develop moulds and machinery suitable to this application. For example, the fluid and polymer channel networks should be designed to guide the fluid and polymer penetration to the extremities of the moulds and cavities without introducing air-traps and gas permeation. Further, the tool and part designs should deliver a balanced filling pattern to minimise uneven fluid and polymer penetration. However these are workshop design matters that will be apparent to a person skilled in the art.

The polymeric resin may be a thermoplastic (i.e. solidify by removal of heat) or thermosetting (i.e. solidify by the addition of heat) resin, provided that it is a property of the polymeric resin that as it solidifies in the mould cavity it does so first at or near the cavity surfaces. In this way, and in the preferred form of the invention, prior to the liquid centre of the polymeric moulding solidifying, it can be blown out of the cavity by fluid injected at high pressure. This forms an orifice from one end of the cannula to the other end. Suitable polymeric resins may therefore be any thermoplastic resin, such as polyamide or polyester, and some thermosetting resins, such as phenolic or epoxy resins. Since most needles need high strength and stiffness, the polymeric resin may be filled with structurally reinforcing fibres such as carbon or glass fibres.

In particular, the polymeric resin may be selected from the group comprising polyethermide, polycarbonate, glass or carbon filled polyester or polyamide and liquid crystal polymers.

The fluid that is passed into the moulding to form the orifice is preferably a gas such as air or nitrogen. However, the fluid may be some other gas that does not react with or contaminate the polymeric resin, that can be injected at such a pressure as to blow out the liquid centre of the moulding to form an orifice. The gas may or may not be heated depending on the polymeric resin. As an alternative to gas a liquid may be used. Further, while it is preferred to inject the fluid to cause the removal of the liquid centre portion of the moulding, the same effect may be provided by applying a suction to the cavity, thus causing the fluid to be drawn therethrough.

Furthermore, the fluid may be injected from either end of the cavity, or may be injected via an intermediate polymer feed channel.

It will of course be appreciated that the present invention relates not only to the method of manufacturing a one-piece integral needle, but also to the moulds for use with the method, and the one-piece integral needles produced by the method. It will also be appreciated that it has been necessary to refer to the one-piece integral needle as having two portions—namely, a cannula and a mounting hub. These are terms that are perhaps more easily assignable to the conventional multi-piece needles that have a metal cannula and a plastic mounting hub. Thus, in this specification, reference to a "cannula" is intended to refer to that portion of the one-piece integral needle that is the tube, at least a part of which will be subcutaneously inserted into a person or animal when used for the injection or removal of fluids therefrom, while reference to a "mounting hub" is that part of the one-piece needle that is immediately adjacent the cannula and is adapted so as to be receivable by a syringe or the like in a fluid-tight engagement.

The invention will now be described in relation to a preferred embodiment as illustrated in the accompanying drawings. However, it must be understood that the following description is not to limit the generality of the above description.

In the drawings:

FIG. 1 is a cross-section through a mould cavity for use with the present invention;

FIGS. 2 to 5 are the same cross-section as illustrated in FIG. 1, but at various stages of the method of the invention;

Figure 6:
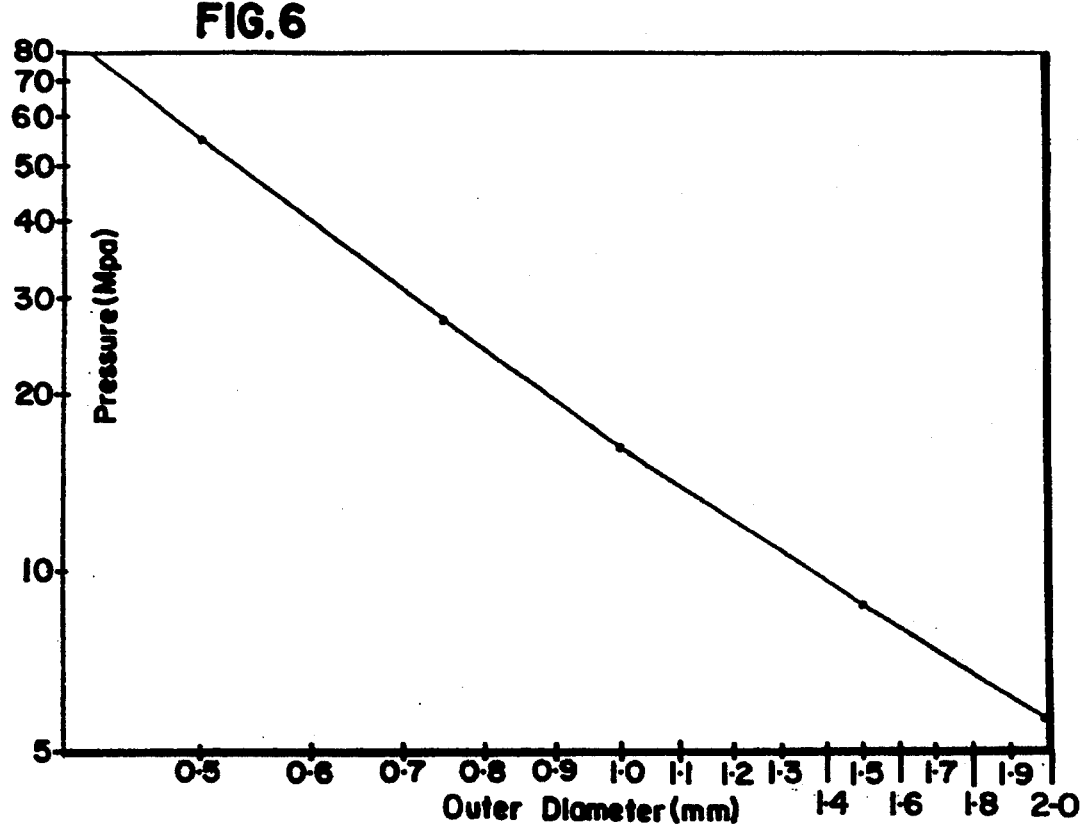

FIG. 6 plots steady state thickness versus needle outer diameter; and

Figure 7:
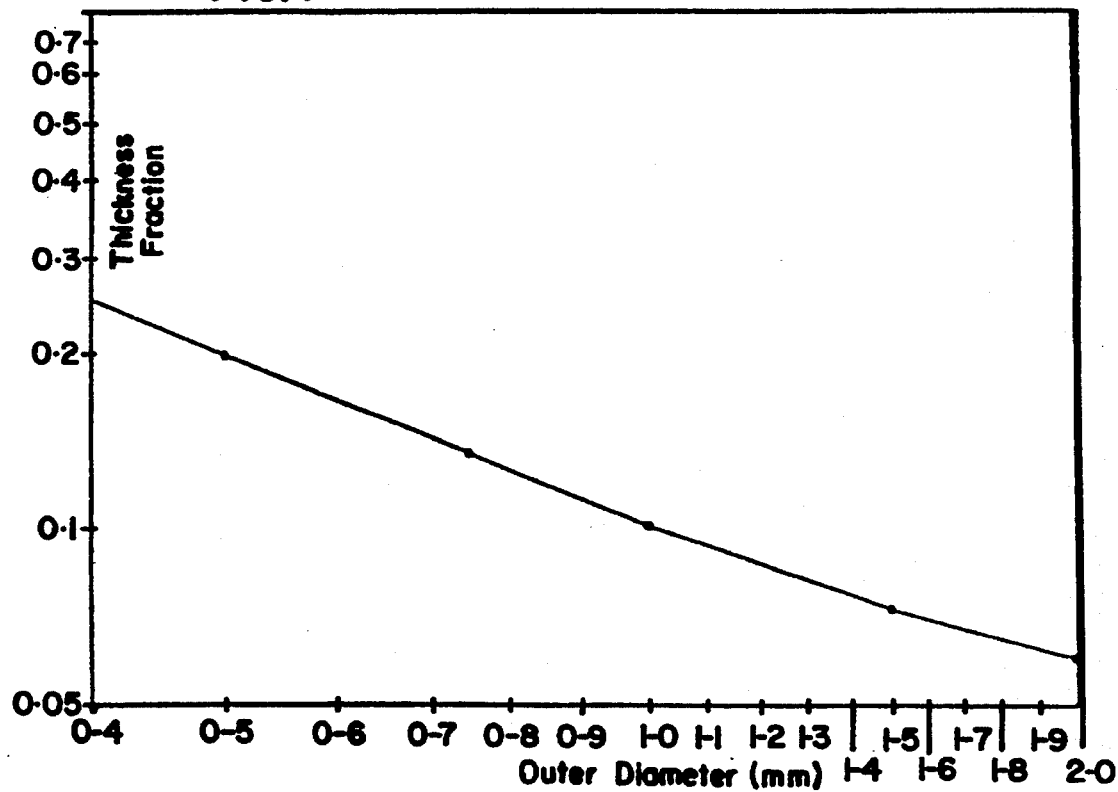

FIG. 7 plots injection pressure versus needle outer diameter.

Referring to FIG. 1, a mould 10 is provided in two halves (12 and 14) and includes therewithin a cavity 16. The cavity 16 is generally in two portions—being a first portion 18 that provides the cannula and a second-portion 20 that provides the mounting hub.

The mould 10 also includes a channel 22 having an inlet 24 and an outlet 26. The outlet 26 is located centrally of the inwardly tapered portion 28 of the second portion 20 of the cavity 16. Thus, by injecting a fluid through the channel 22 the fluid will be fed into the first portion 18 of the cavity 16.

An exit channel 29 emerges at the other end of the cavity 16 so that an excess of liquid polymeric resin can be expelled from the first portion 18 of the cavity 16 when the fluid is injected, to form an orifice in the moulding in that first portion. A mechanical valve (not shown) may be used to open and shut the channel 22 so that polymeric resin does not enter the channel 22. Polymeric resin may be fed into the cavity 16 along runner 30 made on the split line 32 between the two halves (12 and 14) of the mould 10.

The process cycle starts with the two mould halves (12 and 14) being clamped together with force, and having the cavity 16 and all of the channels empty. The two halves (12 and 14) of the mould 10 mate precisely along the split line 32 so that no liquid polymeric resin can escape from the cavity 16. The mechanical valve (not shown) is shut to stop polymeric resin entering channel 22.

Referring to FIG. 2, liquid polymeric resin 34 is then injected along the runner 30 into the cavity 16 under pressure from a moulding machine (not shown). A solidified layer 36 of polymeric resin 34 forms at the cavity surface 38 during the filling of the cavity 16.

Referring to FIG. 3, the flow of polymeric resin 34 is then stopped before the entire cavity 16 is filled, and the mechanical valve in channel 22 is opened such that fluid 37 is injected into the first portion 18 of the cavity 16 which pushes liquid polymeric resin 34 further into the cavity 16. In this respect, the fluid 37 is preferably a gas such as nitrogen.

Figure 4:
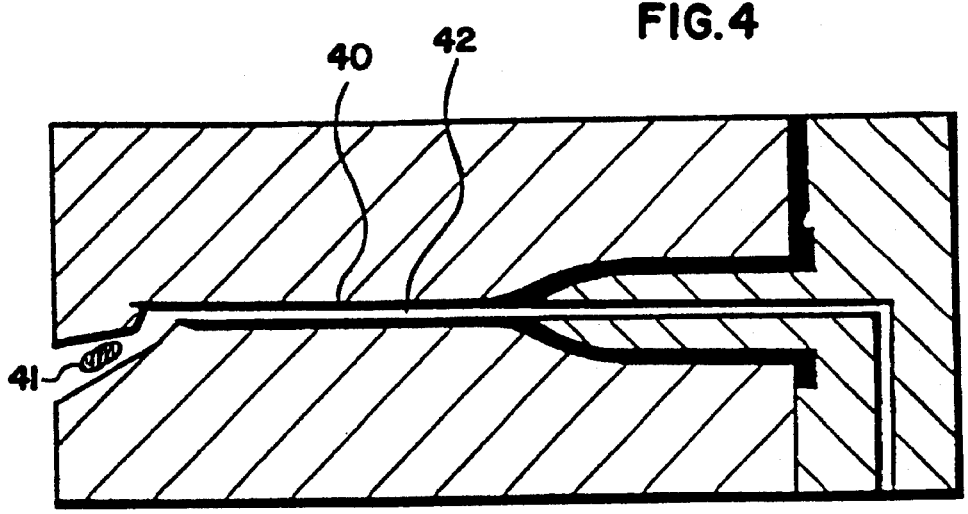

Referring to FIG. 4, the continued injection of fluid pushes liquid polymeric resin to the end of the first portion 18 of the cavity and expels the excess liquid resin 41 through the exit channel 28 at the tip of the mould, leaving an annulus 40 of solidified polymeric resin defining an orifice 42 therethrough.

Figure 5:
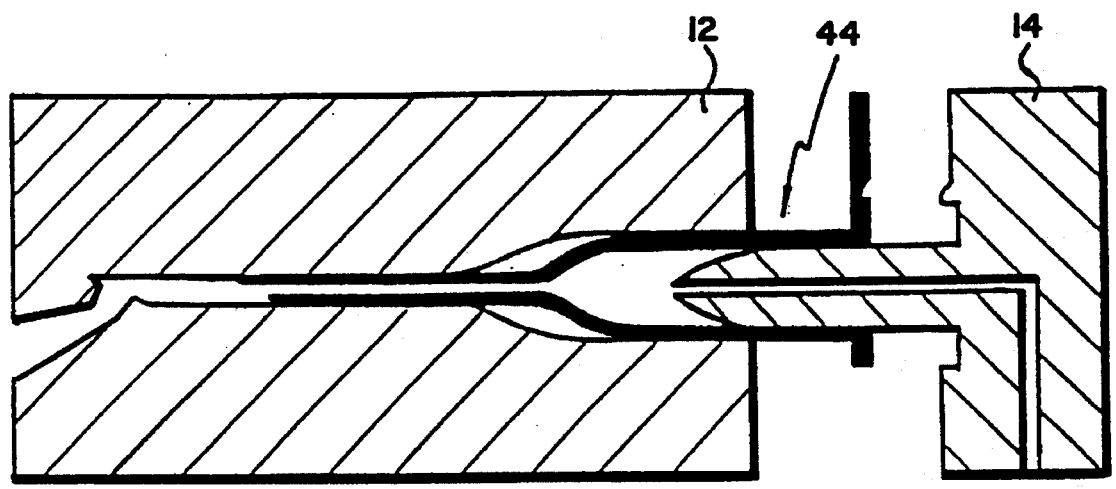

Finally, and in relation to FIG. 5, the two mould halves (12 and 14) are separated and the one-piece integral needle 44 may be removed or ejected by a mechanism in the mould (not shown). The process cycle (represented by FIGS. 2 to 5) may then be repeated. It will also be understood that a plurality of moulds may be provided such that a large number of needles may be produced in a single pass.

Computer simulations have been performed to determine preferred engineering parameters required in moulding very fine needles. A number of materials were evaluated, those being polypropylene, 30% glass filled polyester, polyethermide and polycarbonate. As indicated above, the evaluations revealed that the pressure to mould needles of various diameters was predominantly a function of the materials viscosity.

In particular, the flow of a polymer (the polycarbonate LEXAN 141) in needles 40 mm long and of various diameters was investigated. The moulding conditions used were melt temperature 300° C., mould temperature 20° C. and a flow rate to fill the cannula portion of the cavity in 0.1 seconds. In this respect, it will be appreciated that for other materials, and to produce needles of different dimensions, the operating conditions will require variation. In particular while the flow rate will generally always be such as to fill the cannula in fractions of seconds (to ensure high shear rates between the resin and wall of the mould) the value will require variation as necessary.

The operation of the method of the invention with these parameters, for needles of outer diameters of 2.0, 1.5, 1.0, 0.75 and 0.5 mm, produces moulded product having regions where the thickness of frozen polymer has reached steady state. Here, the heat removed by conduction to a cold mould (freezing the polymer) and the heat added by flow (remelting the polymer) cancel each other and the result is a constant thickness of frozen material. These steady states for the frozen layers assists in allowing the process to be controlled, particularly to assist in setting the internal diameters of the needles.

FIG. 6 shows a plot of these steady state thicknesses versus needle outer diameter. This figure illustrates that for small outer diameters the frozen layer fraction is large (0.05 mm thick for 0.5 mm OD), whereas for large diameters the fraction is small (0.06 mm thick for 2.0 mm OD). It should be noted that a number of moulding parameters can be altered to set and control the frozen layer thickness, including flow-rate, mould temperature, and gas delay time (time before the gas purges molten polymer from inside the frozen layer).

Thus, it is apparent that the method of the invention tends to a steady state and is therefore relatively easy to control. Also, the internal diameters are able to be readily set and frozen layers as thin as 0.05 mm can be produced.

Conventional moulding machines are able to deliver up to 130 MPa injection pressures (some more modern machines up to 180 MPa). FIG. 7 shows that such high injection pressures are not required for the method of the invention, the plot showing that needles of outer diameters smaller than 0.4 mm may be produced by injection pressures lower than 130 MPa.

Further, by introducing various modifications, smaller sized needles may be strengthened, or the conditions may be improved so as to make it possible to produce needles having even smaller outer diameters. In this respect, the cannula is formed from a skin of polymer solidified under high flow-rates, the molecular chains being highly aligned longitudinally along the length of the cannula. Thus, when formed in this way the cannula already is increased in stiffness over the normal properties of the polymer due to the molecular orientation.

However, the stiffness may be increased further by reducing the cannula length (if the length is halved the required pressure is halved), and/or by tapering the diameter of the cannula along its length (if the diameter is doubled, the required pressure is more than halved). Thus, an alternative embodiment of needle produced by this invention is a needle having either a straight or curved taper along its full length, or along only a portion of its length.

This invention thus allows the production of needles in one-piece as a single component and as a single manufacturing process. Conventionally, secondary processes such as gluing and grinding are required and more than one component must be manufactured to form the needle. Thus, the difficulties and expenses in producing needles are reduced through a reduction in the number of components in the needle and the number of manufacturing processes required to make the needle.

In this respect, conventional moulding of a one-piece needle would require a mandrel to be present in the mould, or to be placed into the mould, to form the orifice of the needle. Moulding around such long, small diameter mandrels is very difficult and not suited to mass production. This invention does not require mandrels since injected fluid forms the orifice of the needle. This assists in providing a method where the mould is less expensive and the moulding process is less difficult, thus production of needles by the invention is less expensive than conventional moulding techniques.

Further, needles produced by this invention may also have many new details incorporated into the one-piece moulding. For instance, threads or other fittings for connection to syringes or other dispensing or collecting devices can be incorporated into the one-piece moulding. Other features such as special profiled points, cheers to collect or distribute material from the needle can be incorporated into the one-piece moulding. Thus, the invention allows the production of one-piece needles with additional features incorporated into the design without additional processes or components thus broadening the scope of product design and reducing the expenses and difficulties in manufacturing needles with additional design features.

It will also be understood that there may be other modifications and alterations to the configurations described herein that are also within the scope of the present invention.

We claim:

1. A method for manufacturing an integral one-piece needle having a cannula and a mounting hub, the method being characterized by feeding a molten polymeric resin into a mould having a mould cavity with a cannula forming portion and a mounting hub forming portion extending from the cannula forming portion, allowing a solidified layer of polymeric resin to form adjacent the mold surface of the cannula forming portion of the mould cavity, injecting a fluid under pressure into the cannula forming portion of the cavity to eject a molten central region of the polymeric resin from said cannula forming portion via an exit channel, leaving an annulus of solid polymeric resin having an orifice therethrough, the annulus of polymeric resin forming the cannula of the needle, and allowing soldified polymeric resin to form within said mounting hub forming portion of the mould cavity thereby forming the mounting hub of the needle.

2. A method according to claim 1 wherein the polymeric resin is selected from the group consisting of:
   polyethermide,
   polycarbonate,
   polyester with glass fiber,
   polyester with carbon filler,
   polyamide with glass filler,
   polyamide with carbon filler, and
   liquid crystal polymers.

3. A method according to claim 2 wherein the gas is nitrogen gas.

4. A method according to claim 1 wherein the fluid is injected from either end of the cavity or via an intermediate polymer feed channel.

5. A method according to claim 1, wherein the polymeric resin is fed into the mould cavity along a runner under pressure from a moulding machine, a solidified layer of resin forming on the mould surface, the feeding of resin being discontinued prior to the entire cavity filling, at which time fluid is injected centrally into the cavity to push still molten resin along the orifice created within the central region of the cavity to both create the orifice and to continue the passage of resin along the remaining length of the cavity completing the formation of the solidified layer of resin on the mould surface.

6. A method according to claim 1 wherein the polymeric resin is fed into the mould cavity along a runner under pressure from a moulding machine, a solidified layer of resin forming on the mould surface, the feeding of resin continuing until the entire cavity is filled, at which time the fluid is injected centrally into the cavity to push still molten resin along the orifice created within the central region of the mould to both create the orifice and to continue the passage of resin along the remaining length of the cavity completing the formation of the solidified layer of resin on the cavity surface.

7. A method according to claim 1 wherein the molten injected polymeric resin is at a temperature of about 300° C., the mould temperature is about 20° C., the flow rate of resin is sufficient so as to fill the cavity in about 0.1 seconds, and the injection pressure is less than about 130 MPa.

8. A method according to claim 7 wherein the polymeric resin is polycarbonate.

9. A method according to claim 1 wherein the outer diameter of the cannula increases along its length toward the hub, the increase being constant to provide a straight taper, or gradual to provide a curved taper.

10. A method according to claim 1 wherein the feeding of resin continues until the entire cavity is filled, at which time the fluid is injected centrally.

11. A method according to claim 8 wherein the outer diameter of the cannula increases along its length toward the hub, the increase being constant to provide a straight taper, or gradual to provide a curved taper.

12. A method according to claim 1 wherein the polymeric resin is selected from the group consisting of:
   polyethermide,
   polycarbonate,
   polyester with glass fiber,
   polyester with carbon filler,
   polyamide with glass filler,
   polyamide with carbon filler, and
   liquid crystal polymers.

13. The method of claim 1, further comprising purging the fluid and the molten central region through the exit channel.

14. A method according to claim 6, wherein the fluid is a gas.

15. A method according to claim 14 wherein the gas is nitrogen gas.

* * * * *

UNITED STATES PATENT AND TRADEMARK OFFICE
CERTIFICATE OF CORRECTION

PATENT NO. : 5,620,639

DATED : APRIL 15, 1997

INVENTOR(S) : STEVENS ET AL.

It is certified that error appears in the above-identified patent and that said Letters Patent is hereby corrected as shown below:

Col. 5, lines 49-57, claim 2: delete "A method according to claim 1 wherein the polymeric resin is selected from the group consisting of: polyethermide, polycarbonate, polyester with glass fiber, polyester with carbon filler, polyamide with glass filler, polyamide with carbon filler, and liquid crystal polymers." and insert --A method according to claim 1 wherein the fluid is a gas.--

Col. 6, line 21, claim 6: "mould" should read --cavity--

Col. 6, line 23, claim 6: "cavity" should read --mould--

Signed and Sealed this

Thirtieth Day of June, 1998

Attest:

BRUCE LEHMAN

Attesting Officer

Commissioner of Patents and Trademarks